United States Patent [19]

Schulte et al.

[11] Patent Number: 5,545,205
[45] Date of Patent: * Aug. 13, 1996

[54] UNITARY INTRAVASCULAR DEFIBRILLATING CATHETER WITH BIPOLAR SENSING

[75] Inventors: Theodore J. Schulte, Plymouth; Roger W. Dahl, Andover; Stanley M. Bach, Jr.; J. Edward Shapland, both of Shoreview; Douglas J. Lang, Arden Hills, all of Minn.

[73] Assignee: Cardiac Pacemakers, Inc., St. Paul, Minn.

[*] Notice: The portion of the term of this patent subsequent to Aug. 30, 2011, has been disclaimed.

[21] Appl. No.: 386,210

[22] Filed: Feb. 9, 1995

Related U.S. Application Data

[60] Continuation of Ser. No. 120,188, Oct. 19, 1993, abandoned, which is a division of Ser. No. 753,115, Aug. 30, 1991, Pat. No. 5,269,319, which is a continuation-in-part of Ser. No. 447,908, Dec. 8, 1989, Pat. No. 5,044,375.

[51] Int. Cl.$^6$ .................................................. A61N 1/05
[52] U.S. Cl. .................................................. 607/123
[58] Field of Search ................................ 607/119, 122, 607/123

[56] References Cited

U.S. PATENT DOCUMENTS

| Re. 32,204 | 7/1986 | Halvorsen . | |
|---|---|---|---|
| 3,942,536 | 3/1976 | Mirowski . | |
| 4,156,429 | 5/1979 | Amundson . | |
| 4,289,144 | 9/1981 | Gilman . | |
| 4,318,412 | 3/1982 | Stanly et al. . | |
| 4,332,259 | 6/1982 | McCorkle, Jr. . | |
| 4,355,646 | 10/1982 | Kallok et al. | 607/122 |
| 4,393,883 | 7/1983 | Smyth et al. . | |
| 4,444,195 | 4/1984 | Gold . | |
| 4,481,953 | 11/1984 | Gold et al. | 607/122 |
| 4,499,907 | 2/1985 | Kallok et al. . | |
| 4,559,951 | 12/1985 | Dahl et al. | 607/122 |
| 4,567,900 | 2/1986 | Moore . | |
| 4,567,901 | 2/1986 | Harris . | |
| 4,581,953 | 4/1986 | Walston et al. . | |
| 4,603,705 | 8/1986 | Speicher et al. . | |

(List continued on next page.)

FOREIGN PATENT DOCUMENTS 2157954  8/1987  United Kingdom .

OTHER PUBLICATIONS

"Orthogonal Electrogram Sensing", Goldreyer, et al, PACE, vol. 6, Mar.–Apr. 1983, Part II, pp. 464–469.

Primary Examiner—William E. Kamm
Assistant Examiner—Scott M. Getzow
Attorney, Agent, or Firm—Haugen and Nikolai P.A.

[57] ABSTRACT

A unitary intravascular defibrillating catheter includes distal and proximal spring electrodes, displaced to such distance from one another that defibrillating shock is effected through a field including the interventricular septum and left ventricular free wall. In one embodiment of this catheter, the proximal electrode is placed in the region of the subclavian vein. Alternatively, it may be placed in the region of the third through seventh intercostal space. A unitary catheter is also described which includes an intermediate electrode, placed between distal and proximal electrodes. Selection of placement of electrodes either in the superior vena cava or in the region of the subclavian vein is medically indicated by physiological conditions of the individual patient. The cardioversion system further includes a unipolar or bipolar sensing circuit with at least one sensing electrode, and a cardioversion/defibrillation circuit with either two or three spaced apart spring electrodes. The sensing electrodes are spaced apart from one another, but they are kept sufficiently close to one another for isolated, localized R-wave sensing. The sensing electrodes further are positioned remotely of the cardioversion/defibrillation electrodes, to avoid post-shock abnormalities which otherwise would interfere with a timely R-wave sensing, and to substantially prevent the discharge of an unnecessary cardioversion pulse after return of the heart to normal cardiac rhythm.

38 Claims, 7 Drawing Sheets

U.S. PATENT DOCUMENTS

| | | |
|---|---|---|
| 4,614,192 | 9/1986 | Imran et al. . |
| 4,662,377 | 5/1987 | Heilman et al. . |
| 4,727,877 | 3/1988 | Kallok . |
| 4,735,205 | 4/1988 | Chachques et al. . |
| 4,819,662 | 4/1989 | Heil, Jr. et al. . |
| 4,856,524 | 8/1989 | Baker, Jr. . |
| 4,969,463 | 11/1990 | Dahl et al. . |
| 5,044,375 | 9/1991 | Bach, Jr. et al. . |
| 5,269,319 | 12/1993 | Shulte et al. .......................... 607/122 |

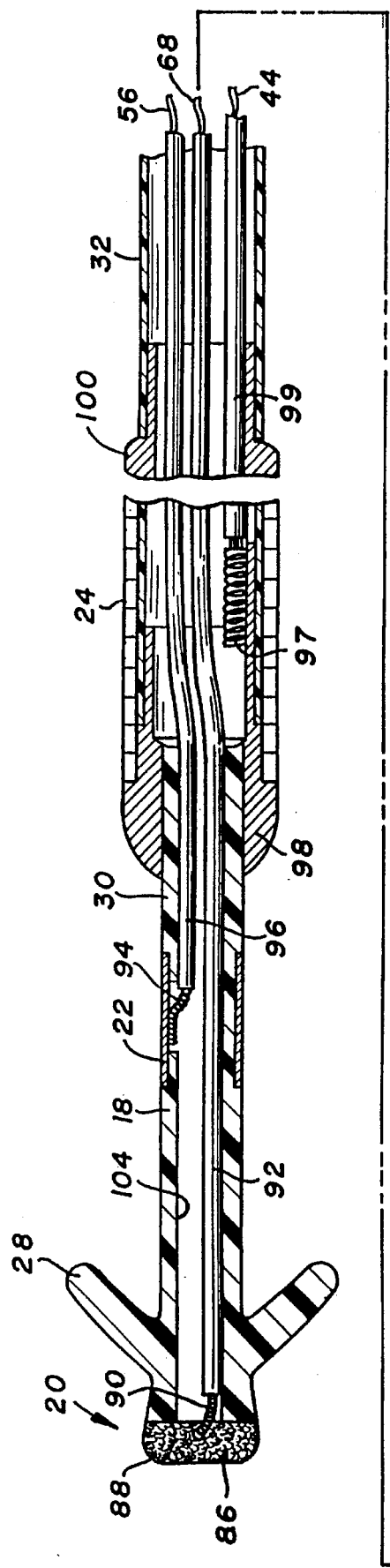
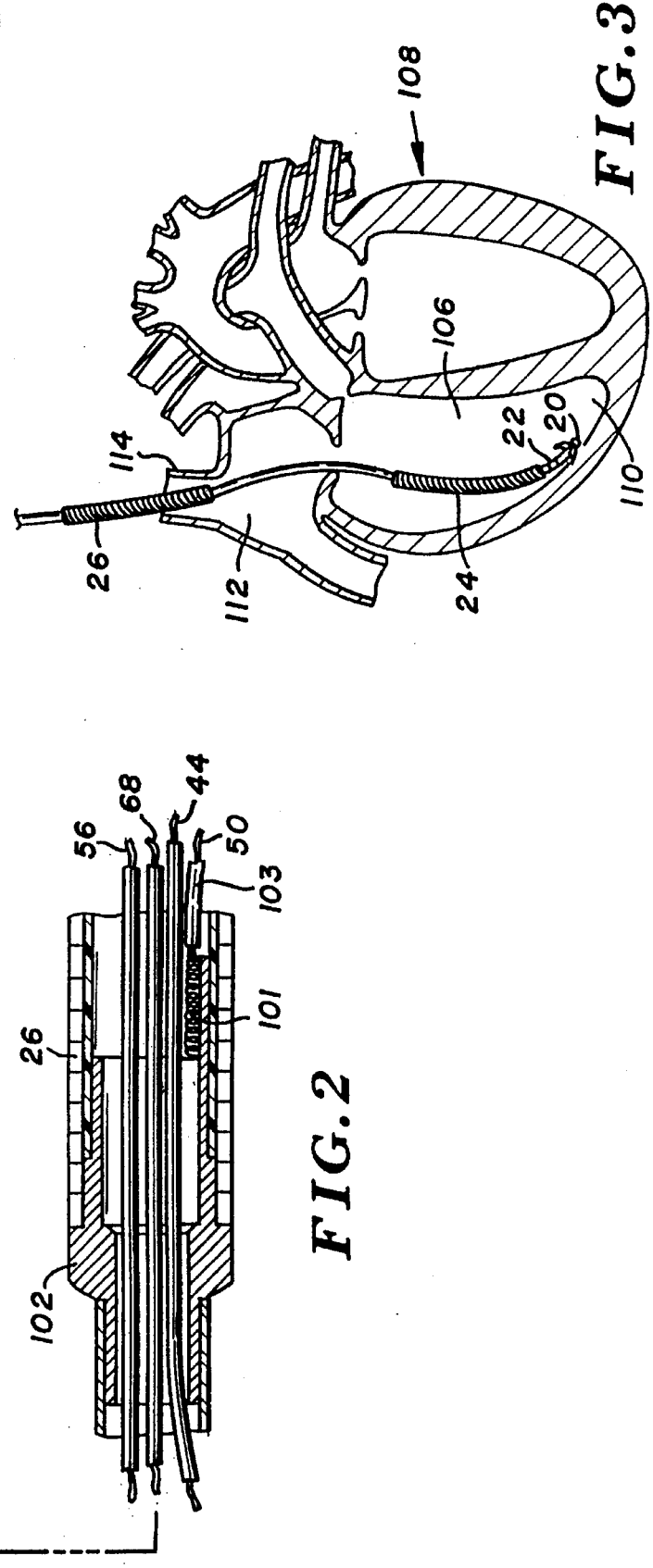

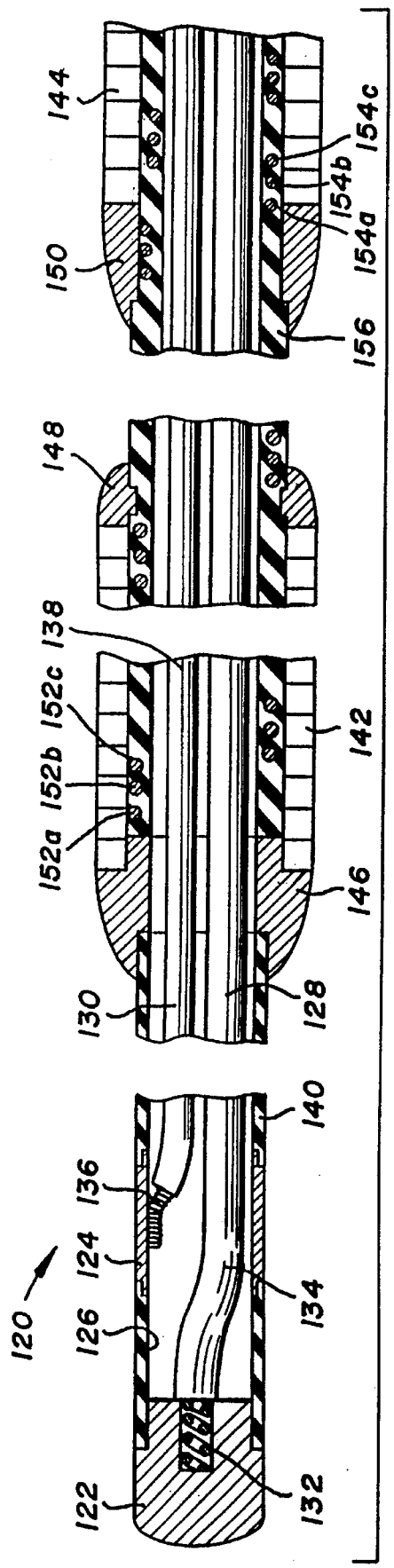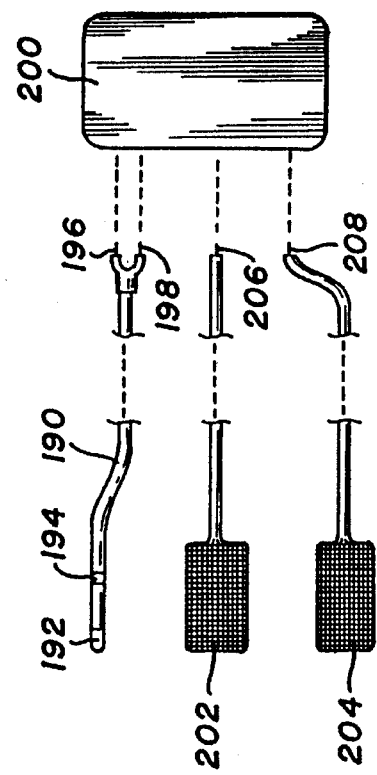
FIG. 4
FIG. 5
FIG. 6

UNITARY INTRAVASCULAR DEFIBRILLATING CATHETER WITH BIPOLAR SENSING

This is a continuation of parent application Ser. No. 08/120,188 filed Oct. 19, 1993, now abandoned, which is a divisional of application Ser. No. 07/753,115 filed Aug. 30, 1991, now U.S. Pat. No. 5,269,319 which is a continuation-in-part of Ser. No. 07/447,908, now U.S. Pat. No. 5,044,375, filed Dec. 8, 1989.

BACKGROUND OF THE INVENTION

This invention relates to body implantable medical devices, and more particularly to defibrillating catheters employing sensing electrodes.

Heart disease is a major cause of death in the United States and in other industrial nations. Tachyarrhythmias (rapid disturbances in cardiac electrical activity), in particular the conditions of ventricular tachycardia and ventricular fibrillation, are widely believed to be the primary cause of sudden deaths associated with heart disease. Atrial tachyarrhythmic conditions, on the other hand, are not considered life threatening unless and until they lead to rapid ventricular disturbance.

Recent experience confirms that tachyarrhythmic conditions frequently can be corrected by applying relatively high energy electrical shocks to the heart, a technique often referred to as cardioversion. Cardioversion devices include implantable electronic stand-by defibrillators which, in response to the detection of an abnormally rapid cardiac rhythm, discharge sufficient energy through electrodes connected to the heart to depolarize and restore the heart to normal cardiac rhythm.

Cardioverting or defibrillaton devices typically include means for monitoring heart activity as well as delivery of cardioversion energy. For example, U.S. Pat. No. 3,942,536 (Mirowski, et al.) discloses an intravascular catheter with an electrode at the distal tip, a distal electrode including a plurality of rings near the tip, and a proximal electrode also consisting of a plurality of rings. The tip and distal electrodes are used to provide pacing pulses, while defibrillation pulses are provided using the distal and proximal electrodes. A probe is provided to sense pressure in the right ventricle, and to initiate cardioversion upon sensing a pressure that does not exceed a predetermined threshold.

U.S. Pat. No. 4,355,646 (Kallok, et al.) is directed to a transvenous defibrillating lead with one tip electrode and three additional, annular electrodes. The tip electrode and the most distal of the annular electrodes are placed in the right ventricle and used to measure impedance changes in the ventricle. Defibrillating pulses are delivered across all four of the electrodes.

A key factor in successful defibrillation by implantable devices is the timely and accurate detection of the R-waves, the electrical signals produced by ventricular contraction. In particular, the sensing means (one or more electrodes) of the defibrillating device must be capable of quickly detecting abnormally high cardiac rhythm in order to trigger the defibrillation pulse. Perhaps more importantly, the sensing means preferably is able to confirm a successful defibrillation, i.e., a return to normal cardiac rhythm, as soon as possible after each defibrillation pulse. Otherwise, there is the danger of the device delivering an unnecessary and possibly harmful defibrillation pulse.

The advantage of preventing unnecessary or undue defibrillation pulses is recognized in U.S. Pat. No. 4,614,192 (Imran, et al.). Imran teaches an implantable cardiac defibrillator employing bipolar sensing, in particular a bipolar sensing electrode assembly including a distal tip electrode and a nearby ring electrode, along with two sensing and high voltage delivery electrodes, one in the superior vena cava and another in the form of a patch over the myocardium, near the apex of the heart. This system contemplates three separately implanted electrodes or groups of electrodes. A unitary intravascular multiple electrode catheter is disclosed in U.S. Pat. No. 4,603,705 (Speicher, et al.). The catheter includes three electrodes: a distal tip electrode, an intermediate spring electrode and a proximal spring electrode. The tip and intermediate electrodes are used in pacing and sensing, while the intermediate and proximal spring electrodes are used to deliver defibrillation pulses.

Use of a common lead for sensing and delivering defibrillation pulses, however, interferes with the timely sensing of R-waves. In particular, tissue proximate the cardioversion discharge electrodes becomes temporarily refractory; that is, it loses much of its ability to conduct electrical impulses immediately after discharge, resulting in an effective suppression and broadening of the R-wave immediately following a defibrillation pulse. Thus, post-shock sensing abnormalities prevent an immediate sensing that the heart has returned to normal sinus rhythm in response to the defibrillation pulse, presenting the risk that another, unneeded and potentially disruptive defibrillation pulse will be delivered.

Therefore, it is an object of the present invention to provide a unitary intravascular implantable device in which post-defibrillation pulse sensing abnormalities are substantially reduced or eliminated.

Another object is to provide an embodiment of a unitary defibrillation catheter with sensing circuitry independent of the defibrillation circuitry and with increased spacing of sensing electrodes from the nearest defibrillation electrode, for more discrete and localized electrograms.

Another object of the invention is to provide an implantable defibrillation device with a defibrillation pulse delivery system with electrodes and conductors suited for relatively high energy defibrillation, along with independent sensing circuitry including electrodes and conductors suited to sensing.

Yet another object is to provide a unitary defibrillation catheter which simultaneously affords optimum spacing between sensing electrodes, between a pair of defibrillation electrodes, and between the most adjacent sensing and defibrillation electrodes.

Still another object is to provide an implantable defibrillation device with a defibrillation pulse delivery system having electrodes displaced on a unitary lead at such distance from one another that the high energy defibrillation pulse is delivered through the myocardial wall to an extracardially positioned electrode.

A still further object is to provide an implantable catheter featuring a unique 3-electrode pulse delivery system contained on a singular lead in which defibrillating pulses are discharged between a distal electrode and at least one electrode placed at predetermined intervals on the lead, spaced to enable one of this pair to be placed in an atrial or supravalvular region, while the other is simultaneously placed either subcutaneously in the region of the third to seventh intercostal space or placed in the region of the subclavian vein.

SUMMARY OF THE INVENTION

To achieve these and other objects, there is provided a unitary intravascular cardioversion device. The device includes an elongate, flexible and dielectric catheter body having a proximal end region, a distal end region and a lumen means formed in the body from the proximal end region to the distal end region. The device has a cardioversion circuit including a cardioversion electrode means mounted on the catheter body proximally of the distal region, and a flexible conductor means connected to the cardioversion electrode means, for conducting electrical pulses between the cardioversion electrode means and the proximal end region, and a cardioversion connector means near the proximal end region for electrically coupling the conductor means with a cardioversion pulse generating means, thereby to deliver cardioversion pulses to the cardioversion electrode means. The device further includes a cardiac sensing circuit. The sensing circuit may include a first sensing electrode mounted on the catheter body at the distal end region, a first sensing conductor means connected to the first sensing electrode for detecting electrical pulses between the first sensing electrode and the proximal end region, a second sensing electrode mounted on the catheter body at the distal end region proximally of the first sensing electrode and spaced apart from the first sensing electrode by a predetermined first distance, a second flexible sensing conductor means connected to the second sensing electrode for detecting electrical pulses between the second sensing electrode and the proximal end region, and a sensing connector means near the proximal end region for electrically coupling the first and second sensing conductor means with a pulse sensing means, thereby to utilize the first and second sensing electrodes as a bipolar pulse sensing pair independent of the cardioversion circuit. Alternatively, the cardiac sensing circuit may include a conventional unipolar circuit having a sensing electrode in electrical communication with the defibrillation control unit.

Preferably, the first sensing electrode is a distal tip electrode at the distal end of the catheter body, and the second sensing electrode is a ring electrode surrounding the catheter body and spaced apart from the tip electrode at a distance in the range of from one to twenty millimeters, preferably at 5 millimeters.

The cardioversion means advantageously includes distal and proximal cardioversion electrodes in the form of flexible, electrically conductive coils. In this event, the conductor means includes a first cardioversion conductor coupled to the distal conversion electrode and a second cardioversion conductor coupled to the proximal electrode. Both cardioversion conductors are flexible and contained in the lumen means, with the cardioversion connector means then coupling both cardioversion conductors to the pulse generating means. Each of the proximal and distal cardioversion coils can have a length in the range of from 1 to 7.5 centimeters.

The preferred spacing between the proximal sensing electrode or ring electrode, and the distal defibrillating electrode, is at least 0.5 centimeter. This ensures that heart tissue proximate and between the sensing electrodes is effectively isolated from the tissue subject to the defibrillation pulse. As a result the device affords accurate R-wave sensing immediately after applying a defibrillation pulse, substantially eliminating the possibility of charging for and delivering unnecessary defibrillation pulses after the heart has returned to normal sinus rhythm.

A further advantage of the present invention is that it permits selection of the distance between the defibrillating electrodes for a preferred positioning of the distal defibrillating electrode, e.g., in the right ventricle near the apex, and of the proximal defibrillating electrode, e.g., high in the right atrium, within the superior vena cava, within the subclavian vein, proximal to the point of insertion in the subclavian vein, or subcutaneously in the region of the third through seventh intercostal space. In certain embodiments, total electrical independence of the sensing system from the defibrillation circuit permits simultaneous optimum separation of the tip and ring electrodes, the ring electrode and distal defibrillating electrode, and the two defibrillating electrodes, an advantage not attainable when a single electrode is utilized for defibrillation pulsing and sensing. An alternative embodiment of the present invention features a pair of defibrillating electrodes on a unitary lead in which the proximal electrode is placed at such distance from the distal (apical) electrode that discharge from the distal electrode develops a field between distal and proximal electrodes. When the proximal electrode is placed subcutaneously, this field includes the interventricular septum and the left ventricular free wall. When the proximal electrode is placed within or near the subclavian vein, this field includes the left atrium as well as the interventricular septum and the left ventricular free wall. In the prior art, this field was positioned intracavitarily between the right ventricular apex and the right atrium or the superior vena cava.

Alternatively, the cardioversion/defibrillation means includes three flexible electrically conductive coils, spaced at predetermined distances from one another, each coupled to flexible conductors contained in the lumen means and connected to a pulse generating means. Each coil is dimensioned and spaced as in the accompanying embodiments, with the placements being generally apical, supraventricular or subclavian, and intercostal. Selection of placement of electrodes is medically indicated by physiological conditions of the individual patient.

Yet another advantage of the present invention resides in the ability to tailor electrodes and conductors specifically for the sensing system, and to tailor other electrodes and conductors specifically for the defibrillation circuit. The relatively high currents and voltages involved in the defibrillation circuit require electrodes having relatively large surface area in order to reduce impedance, and using conductors formed of drawn brazed strand (DBS) wires or other highly conductive material. The sensing system does not impose these requirements as stringently. A unitary catheter with independent sensing and cardioversion systems, in accordance with the present invention, permits a better impedance matching of the two sensing electrodes. Such catheter further allows selection of materials and component sizes customized to either sensing or cardioversion, for example, multi-conductor tube (MCT) construction involving coaxial windings for defibrillation conductors, in combination with sensing conductors contained within a central lumen of the catheter.

Another aspect of the present invention is a cardioversion and sensing system in which sensing electrodes are mounted on a sensing catheter for use in conjunction with a pair of cardioversion electrodes. The cardioversion electrodes may be provided as coils on a separate cardioversion catheter, as two separate patch electrodes, or as a single defibrillation coil in combination with either a patch electrode or a subcutaneous array, as described in applicant's co-pending application serial number 07/533,886. The electrodes are placed in the region of the heart, encompassing ventricular and atrial endocardial placement, intrapericardial or extrapericardial placement, vascular positioning, and in general within or about the thoracic cavity, including the subclavian region. Additional placement sites include various subcutaneous intercostal placements. The subcutaneous site is generally in the region of the third to seventh intercostal space, as determined by the physiology of the individual patient. The use of patch electrodes for cardioversion, alone or with a coil electrode, affords a high degree of flexibility in electrode positioning.

Thus, in accordance with the present invention, a catheter system provides sensing electrodes in complete isolation from a defibrillation pulse delivery system, for substantially immediate R-wave sensing following the application of each defibrillation pulse.

IN THE DRAWINGS

For a further understanding of the above and other features and advantages, reference is made to the following detailed description and the drawings, in which:

FIG. 2 is a sectional view of a portion of the catheter of FIG. 1;

FIG. 3 is a sectional view illustrating the positioning of the catheter of FIG. 1 within the heart;

FIG. 4 is a sectional view of a portion of an alternative embodiment catheter constructed in accordance with the present invention;

FIG. 5 is a plan view of another alternative embodiment of the invention comprising two leads separately implanted in the heart;

FIG. 6 is a schematic view of yet another alternative embodiment using patch electrodes for defibrillation;

DETAILED DESCRIPTION OF THE PREFERRED EMBODIMENT

Figure 1:
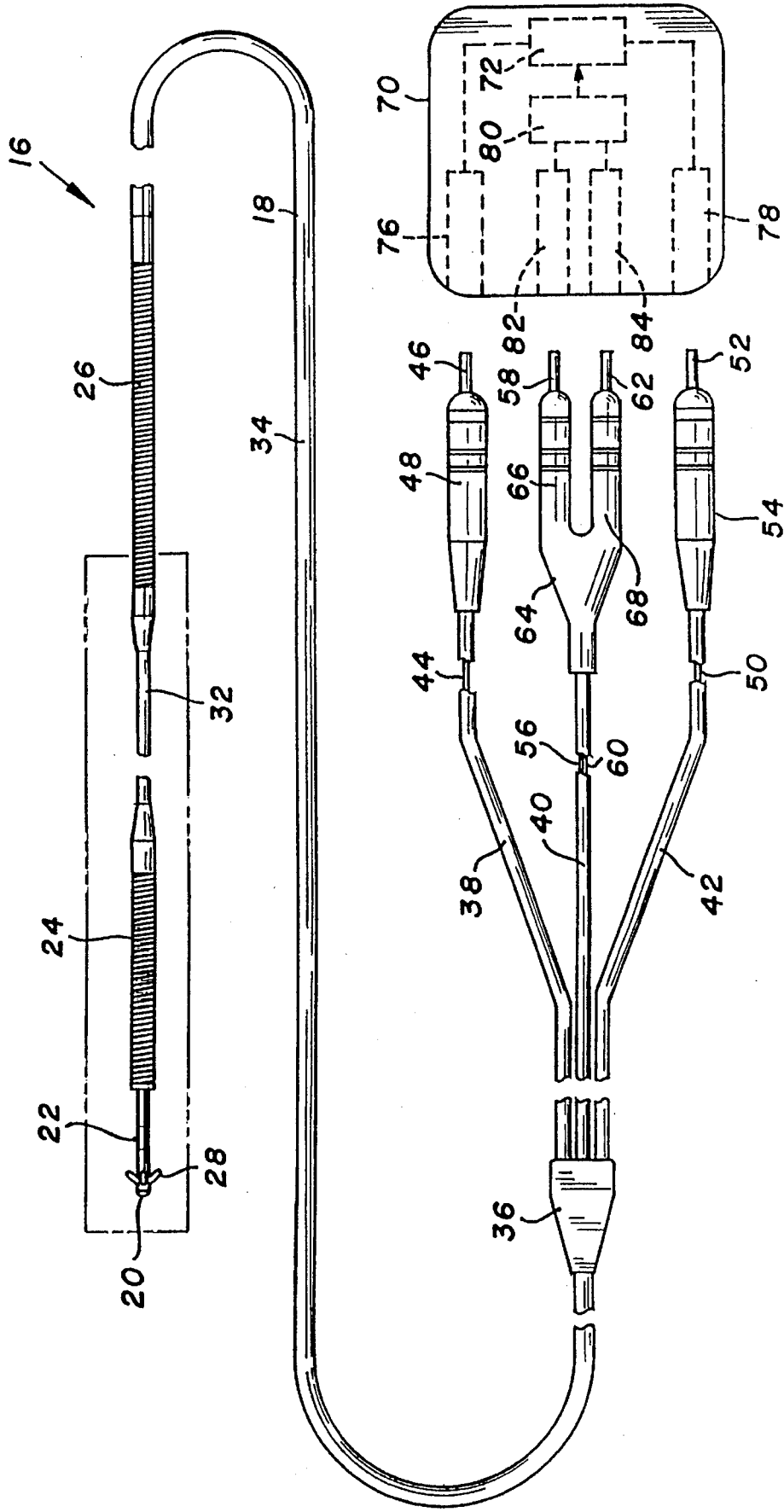
FIG. 1 is a plan view of a unitary intravascular defibrillating catheter constructed in accordance with the present invention.

Turning now to the drawings, there is shown in FIG. 1 a unitary intravascular defibrillation/cardioversion catheter 16 including an elongate and flexible catheter body 18 constructed of a dielectric material, for example, silastic or polyurethane. Four electrodes are mounted to the catheter body, including a distal tip electrode 20 at the distal end of the body, a bipolar ring electrode 22, a distal spring electrode 24 and a proximal spring electrode 26. A plurality of tines 28 near the distal end of the catheter, formed of the dielectric material comprising the body, assist in the positioning and securing of the catheter during implant.

Catheter body 18 further includes a reduced diameter distal tubing portion 30 which supports the tip and ring electrodes, a proximal reduced diameter tubing portion 32 between spring electrodes 24 and 26, and a sheath portion 34 encompassing the majority of the catheter length.

A reinforcing member 36 provides a junction for sheath 34 and three lengths of electrically insulative tubing 38, 40 and 42. Tubing 38 contains a conductor 44 provided for transmitting electrical signals from distal spring electrode 24 to a pin 46. An electrically insulative boot 48 surrounds pin 46 and tubing 44. A conductor 50, contained within insulative tubing 42 and sheath 34 electrically couples proximal spring electrode 26 and a pin 52, with pin 52 and tubing 42 being surrounded by an electrically insulative boot 54.

Similarly, a conductor 56 electrically couples ring electrode 22 with a pin 58, and a conductor 60 similarly couples tip electrode 20 with a pin 62. Pins 58 and 62 and conductors 56 and 60 are surrounded by an insulative plug 64 with boot portions 66 and 68.

In use, catheter 16, particularly at plug 64 and boots 48 and 54, is electrically and mechanically coupled to a defibrillation control unit 70 including defibrillation pulse generating circuitry 72, represented schematically in FIG. 1. Unit 70 includes a pair of receptacles 76 and 78 for receiving pin 46 and boot 48, and pin 52 and boot 54, respectively, thus to electrically couple spring electrodes 24 and 26 with defibrillation pulse generating circuitry 72. Boots 48 and 54 fit tightly within their respective receptacles to provide a positive fluid seal.

Defibrillation unit 70 further includes pulse or heart rate sensing circuitry represented schematically at 80. A pair of sensing receptacles 82 and 84 receive plug 64, to electrically couple distal tip electrode 20 and ring electrode 22 with the sensing circuitry, with the boot portions of the plug member again providing a fluid seal. Further details of defibrillation control unit 70 are not discussed herein as they are known in the art and not particularly germane to the present invention. In short, the connection of pins 46, 52, 58 and 62 as described creates two independent electrical circuits: a sensing circuit including tip electrode 20 and ring electrode 22, and a defibrillation circuit including spring electrodes 24 and 26. Alternatively, a conventional unipolar sensing circuit may be used, including a single sensing electrode (not shown) mounted on a catheter body, such as catheter body 18, and positioned to lie within the right ventricle during use. This unipolar sensing is directed to the defibrillation unit 70, in the conventional manner. The sensing circuit monitors heart electrical activity, in particular to sense tachyarrhythmias. In response to such sensing, the pulse generating circuit delivers a defibrillating pulse to the heart across spring electrodes 24 and 26.

As seen in FIG. 2, tip electrode 20 is constructed of one or more filaments, preferably a thin wire 86 of platinum or a platinum iridium alloy. The wire is stretched, then crumpled and packed against the distal end of catheter body 18. A screen 88, also of platinum or a platinum alloy, is fastened to the periphery of the catheter body distal end and maintains the crumpled wire in place. For further information regarding this type of electrode, reference is made to U.S. Pat. No. 4,156,429 (Amundson). So constructed, electrode 20 is highly porous, for example, consisting of approximately twenty percent platinum alloy by volume, the remaining eighty percent being open to permit passage of bodily fluids through the tip electrode and to admit ingrowth of tissue, which assists in anchoring the tip electrode after implant. Tip electrode performance may be further enhanced by surface treatment to micro texturize the tip, as disclosed in U.S. Patent application Ser. No. 325,764, filed Mar. 20, 1989, and assigned to the assignee of this application. This treatment substantially increases the reactive surface area of the tip.

Conductor 60 (FIG. 1) includes a multifilar coil winding 90 formed of a nickel alloy or other electrically conductive material permitting flexure. The exposed distal end of coil 90 is electrically and mechanically coupled to distal tip electrode 20. The remainder of the coil is surrounded by a flexible, dielectric sheath 92, within which coil 90 is electrically coupled to conductor 68. The remaining conductors are similarly constructed. Conductor 56 includes a multifilar coil winding 94 surrounded by a sheath 96 and with its exposed distal end coupled to ring electrode 22. The ring electrode 22 is constructed of platinum, a platinum iridium alloy or other appropriate electrically conductive and body compatible material. The outer surface area of the ring electrode exposed to bodily tissue and fluids is in the range of from ten to one hundred square millimeters, and more preferably is about the same in effective surface area as the tip. If desired, ring electrode 22 can be subject to sputtering or other surface treatment to impart microporosity. For accurate R-wave sensing, ring electrode 22 must be spaced apart from tip electrode 20 in the range of from one to twenty millimeters, with a particularly preferred spacing between these electrodes being about ten millimeters.

Proximally of ring electrode 22 is a fitting 98 which surrounds distal tubing portion 30. Fitting 98 is joined to the distal end of spring electrode 24, and cooperates with a fitting 100 at the proximal end of spring electrode 24 to support the electrode. A multifilar coil 97 formed of nickel alloy or other flexible conductor is mechanically and electrically coupled between spring electrode 24 and conductor 44 within flexible dielectric sheath 99. Distal spring electrode 24 can have a length of from 1 to 7.5 centimeters, and up to 15 centimeters, if especially smooth. Preferably electrode 24 is 6 centimeters long, to provide a relatively large exposed surface area necessary for effective delivery of defibrillation pulses. Spring electrode 24 is spaced apart from ring electrode 22 a distance in the range of five to thirty millimeters, although generally a spacing of at least one centimeter is recommended to ensure that heart tissue used in sensing pulse rate, particularly tissue near ring electrode 22, is sufficiently distant from tissue affected by the defibrillation pulse to ensure a localized, isolated and therefore more accurate R-wave sensing.

Proximally of spring electrode 24, a pair of fittings, one of which is shown at 102, support proximal spring electrode 26. Like spring electrode 24, spring electrode 26 is constructed of an electrically conductive and bodily compatible material such as titanium or platinum and mechanically and electrically connected to flexible coil winding 101. Coil winding 101 is mechanically and electrically affixed to conductor 50 within dielectric sheath 103. Proximal spring electrode 26 can have a length in the range of 1 to 7.5 centimeters, and is preferably 4.8 centimeters long. The spacing between proximal and distal spring electrodes 24 and 26 preferably is about eleven centimeters, although a spacing of from six to fourteen centimeters has been found satisfactory.

Tubing sections 30 and 32, spring electrodes 24 and 26 and sheath 34 cooperate to define a central lumen 104 running the length of the catheter from the distal tip to reinforcing member 36. Conductors 44, 50, 56 and 60 all are contained within lumen 104. Proximally of reinforcing member 36 (FIG. 1), each of the conductors is contained within its corresponding one of tubing sections 38, 40 and 42. Thus, the proximal tubing sections sheath, spring electrodes, and distal tubing sections form a lumen means in which the conductors are contained and thus isolated from bodily fluids.

Catheter 16 is inserted intravenously, for example, into the subclavian vein or the cephalic vein, and progressively moved toward the heart until the distal end reaches a selected cardiac chamber. As illustrated in FIG. 3, catheter 16 preferably is inserted to position distal tip electrode 20 and ring electrode 22 in the right ventricle 106 of the heart 108, near the apex 110. Within the ranges for spacing and lengths discussed above, spring electrode 24 preferably is within the right ventricle when tip electrode 20 is positioned as described, with proximal spring electrode 26 located high in the right atrium 112 or in the superior vena cava 114.

With the distal tip positioned as shown, the lead proximal end, still outside the body, is maneuvered to implant the distal tip into the endocardium. Once implanted, distal tip electrode 20, ring electrode 22, conductors 56 and 50 and sensing circuitry 80, cooperate to monitor electrical activity in the heart, in particular R-wave activity.

FIG. 4 shows an alternative design catheter 120 with a solid platinum or titanium tip electrode 122 and an annular electrode 124 near the tip electrode for bipolar R-wave sensing. A central lumen 126 of catheter 120 contains a pair of conductors 128 and 130 connected to tip electrode 122 and annular electrode 124, respectively. Conductor 128 includes a conductive multifilar coil winding 132 surrounded by an insulative sheath 134 and exposed at its distal end for connection to the tip electrode. Similarly, conductor 130 includes a coil winding 136 surrounded by an insulative sheath 138 and exposed for its connection to the annular electrode. Electrodes 122 and 124 are mounted on a dielectric and flexible distal tubing section 140 of catheter 120.

Defibrillation pulses are applied through a pair of spring electrodes, a distal spring electrode 142 and a proximal spring electrode 144. The distal spring electrode is supported between a pair of fittings 146 and 148 at its opposite ends. Spring electrode 144 is similarly supported between a pair of fittings, one of which is shown at 150.

For transmission of cardioversion pulses between spring electrodes 142 and 144, multi-filament conductors 152 and 154 are connected to electrodes 122 and 124, respectively, and also are electrically coupled to a pulse generator, not shown. Each of conductors 152 and 154 includes a plurality of individual electrically conductive filaments arranged in parallel, helical paths about the center of catheter 120. More particularly, conductor 152 includes filaments 152a, 152b and 152c, embedded in a length of insulative tubing 156 and thus electrically isolated from one another. At their distal ends, however, filaments 152a–c are exposed for electrical coupling to distal spring electrode 142.

Similarly, conductor 154 includes filaments 154a, 154b and 154c. Through the majority of the length of conductor 154, the filaments are embedded in tubing 156 and thus are electrically isolated. The distal ends of the filaments are exposed near electrically conductive fitting 150, for electrical coupling to this fitting, illustrated as an alternative to a coupling of these filaments to spring electrode 144. Conductors 152 and 154 are laterally offset from one another over the entire length of tubing 156 and thus are electrically isolated from one another. The multi-filament construction of these conductors affords the desired flexibility in catheter 120 and the increased cross-sectional conductive area desired for handling high energy cardioversion pulses, while permitting the catheter diameter to remain relatively small. For a further explanation of the helically wound and isolated filament technique, reference is made to U.S. Pat. No. 4,559,951 (Dahl, et al.).

FIG. 5 discloses yet another approach to separate sensing and defibrillating, employing a sensing catheter 160 and a defibrillation catheter 162, separately implantable within the right ventricle 164 of the heart 166. Sensing catheter 160 includes a tip electrode 168 and a ring electrode 170 near the distal tip but separated from the tip electrode by one to ten millimeters as previously explained. A pair of conductors, contained within insulative tubing 172, connect tip and ring electrodes 168 and 170 with pulse sensing circuitry near the proximal end of sensing catheter 160. Defibrillation catheter 162 includes a distal tip with tines 174 to assist in positioning the catheter upon implant. Proximal and distal spring electrodes 176 and 178 are mounted to catheter tubing 180 as explained in connection with FIGS. 2 and 4. A pair of conductors, one associated with each of spring electrodes 176 and 178, transmit defibrillation pulses to the spring electrodes. The conductors may be contained in a central lumen of the catheter, or alternatively helically wound as explained in connection with FIG. 4. The sensing and defibrillating conductors are coupled to pulse generating and heart rate sensing circuitry by plugs 182 and 184, respectively. If desired, a patch electrode 186, at least equal to spring electrodes 176 and 178 in surface area, is secured to myocardial tissue and used in combination with the spring electrodes or in lieu of one of the spring electrodes. As compared to the embodiments in FIGS. 2 and 4, the two-catheter system in FIG. 5, of course, requires a greater degree of skill and effort for implantation. On the other hand, it affords the added advantage of lateral or transverse orientation of the sensing electrodes from the defibrillation spring electrodes, to assure localized R-wave sensing remote from tissue subject to defibrillation trauma, and further to permit optimum positioning of the sensing system and the defibrillation system, each fully independently of the other.

FIG. 6 schematically illustrates a system employing a sensing catheter 190 having a tip electrode 192 and a ring electrode 194 spaced apart from the tip electrode by one to ten millimeters. A pair of conductors in the catheter are connected at their distal ends to electrodes 192 and 194, respectively, and at their proximal ends to pins 196 and 198. The pins are plugged into a defibrillation control unit 200 similar to unit 70 described in connection with FIG. 1, to electrically couple the sensing electrodes to sensing circuitry in the control unit.

The system further includes a pair of defibrillation electrodes in the form of patch electrodes 202 and 204, each of which is subcutaneously implanted in the thoracic region, e.g., secured to myocardial tissue. A conductor electrically couples patch electrode 202 with a proximal pin 206, and another conductor likewise couples patch electrode 204 to a proximal terminal pin 208. Pins 206 and 208 are plugged into control unit 200 to electrically couple the patch electrodes with a pulse generating circuit contained in the control unit.

In this system, catheter 190 is provided solely for sensing and defibrillation is accomplished solely through the patch electrodes. Accordingly, this system is particularly useful in applications calling for maximum flexibility in the positioning of defibrillation electrodes, and in which a single catheter is preferred.

Figure 7:
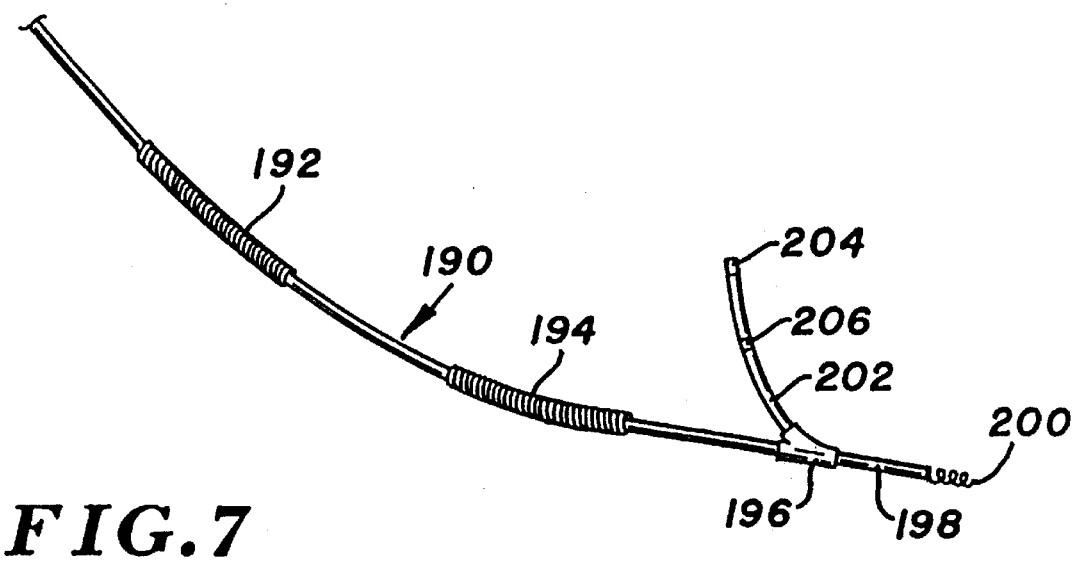
FIG. 7 is a plan view of an alternative embodiment of a unitary intravascular defibrillating catheter constructed in accordance with the present invention.
Figure 8:
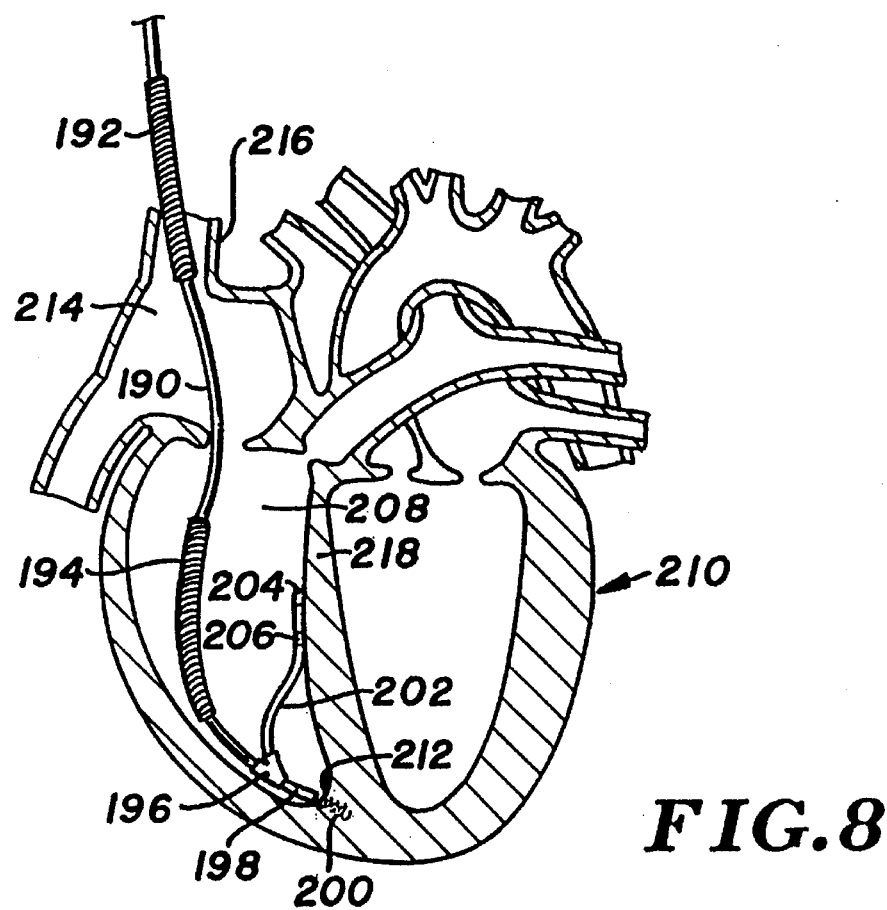
FIG. 8 is a sectional view illustrating the positioning of the catheter of FIG. 7 within the heart.

FIGS. 7 and 8 illustrate another alternative, namely a catheter 190 having a proximal spring cardioversion electrode 192, a distal spring cardioversion electrode 194 and a bifurcated tip at junction 196. Separate conductors (not shown) are connected to spring electrodes 192 and 194, respectively, for transmitting cardioversion pulses between these electrodes. Near the distal end of catheter 190, an insulative boot forms a junction 196. A first extension 198, distally of the junction, supports a helical coil 200 used in a known manner to secure extension 198, and thus the remainder of the lead, to endocardial tissue.

A second extension 202 of the catheter is directed generally proximally of junction 196 but inclined relative to the remainder of the catheter. Two sensing electrodes, including a tip electrode 204 and a ring electrode 206, are supported on extension 202 and constructed as previously described. Separate conductors are connected to tip electrode 204 and ring electrode 206, respectively, each for transmitting electrical pulses between its associated sensing electrode and the proximal end region of catheter 190.

As seen in FIG. 8, catheter 190 preferably is inserted to position the distal tip of extension 198 in the right ventricle 208 of the heart 210, at the apex 212. Coil 200 is secured to endocardial tissue at the apex and thus maintains catheter 190 in the desired position. As noted previously in connection with other embodiments, distal spring electrode 194 preferably is within the right ventricle and proximal spring electrode 192 is in either the right atrium 214 or the superior vena cava 216.

Extension 202 of the catheter is inclined away from the remainder of catheter 190 toward the septum 218, preferably to positioned tip electrode 204 and ring electrode 206 against the septum along the outflow tract, again resulting in remote sensing of the area subject to cardioversion pulses. In view of the reverse bend in the conductors from the sensing electrodes at junction 196, it is recommended that these conductors be coils, with a known reverse winding technique used to negotiate the relatively sharp bend. In other respects, the electrodes and conductors can be constructed as previously described.

Figure 9:
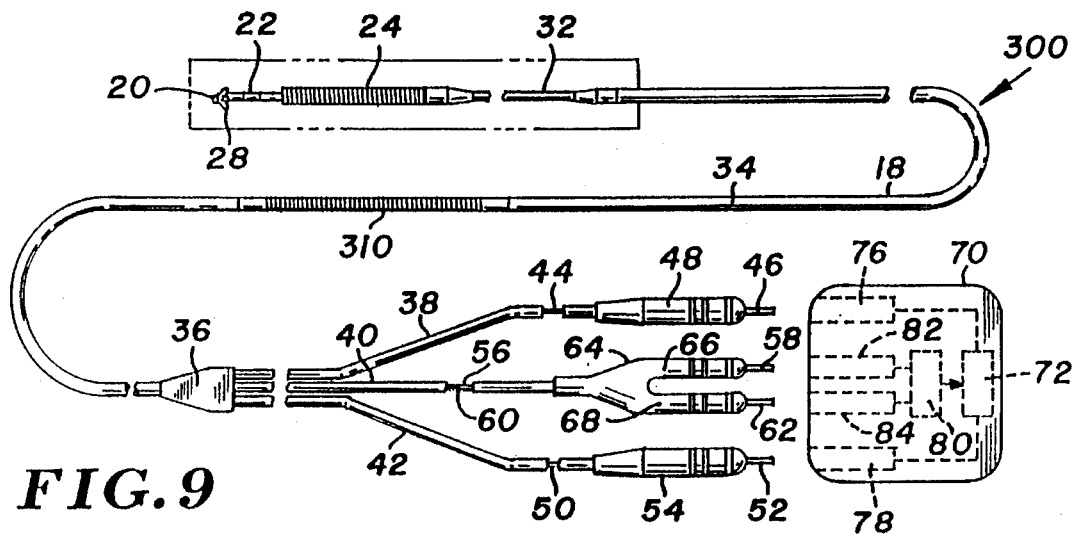
FIG. 9 is a plan view of yet another alternative embodiment of the unitary intravascular defibrillating catheter constructed in accordance with the present invention.
Figure 10:
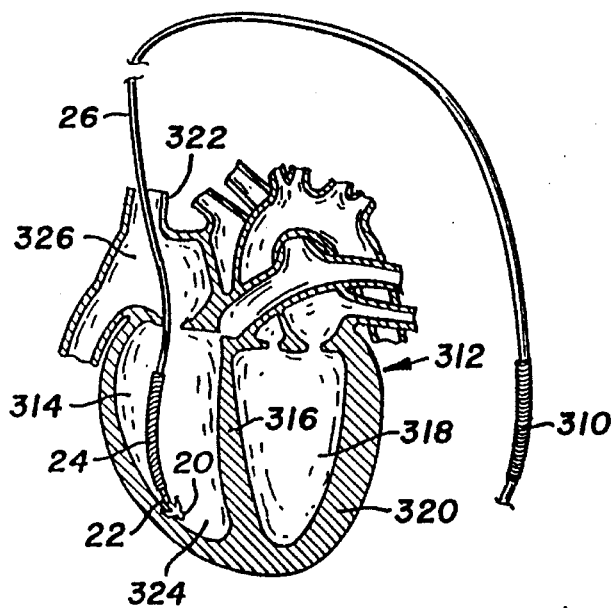
FIG. 10 is a sectional view of the placement of the catheter of FIG. 7 within and about the heart.
Figure 11:
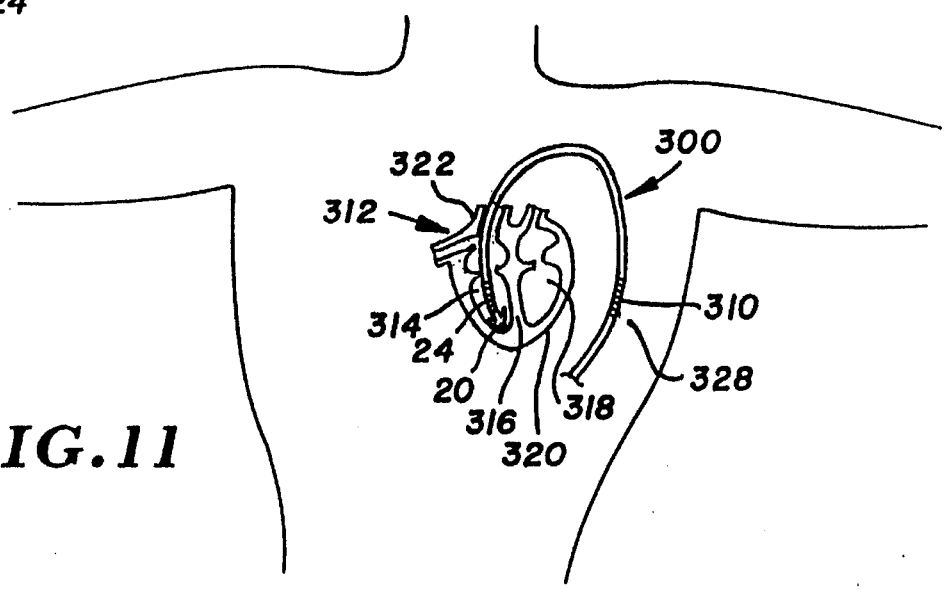
FIG. 11 is a sectional view illustrating the unitary intravascular defibrillation catheter of FIG. 9 in situ.

FIGS. 9, 10 and 11 illustrate a variation of the embodiment shown in FIGS. 1 and 3, in which the proximal electrode is located in the range of approximately 30 to 100 cm from the tip electrode 20. Generally designated as 300, a unitary intravascular defibrillation catheter having a proximal spring cardioversion electrode 310 is positioned subcutaneously approximately in the region of the third through seventh intercostal space (FIG. 11), similar to the placement of a subcutaneous patch electrode. Placement is determined by the anatomy of the patient, with the sixth intercostal space representing typical positioning within a range of the third through the seventh intercostal space. This positioning enables a cardioverting or defibrillating shock to develop a field between distal spring electrode 24 and spring electrode 310. When spring electrode 310 is placed subcutaneously as described above and spring electrode 24 is placed in heart 312 so it is positioned within the right ventricular cavity 314, this field includes the right ventricular cavity 314, interventricular septum 316, left ventricular cavity 318 and left ventricular free wall 320. As in FIG. 3, the unitary intravascular defibrillation catheter 300 is introduced through the superior vena cava 322 and anchored within the right ventricular cavity 314 using a plurality of distal tines 20, which hook around the papillary muscle (not shown) near the right ventricular apex 324.

It should also be noted that the proximal placement of the spring electrode 310 in the region of the third through seventh intercostal space shortens the length of conductor 50 and insulative tubing 34. This results in a distal lead body of reduced diameter for a much greater length than that required by the embodiment of FIG. 3. The primary benefit of this feature is seen during the surgical procedure to insert the lead 300. In a typical procedure, the subclavian vein (not shown) is exposed in the region of the shoulder. The lead 300 is inserted within the lumen of this vein and the tip 20 is advanced within the superior vena cava 322 and right atrium 326 and into the right ventricle 314. The wall of the subclavian vein is sutured around the lead 300 at the insertion point, then the remaining proximal end of the lead 300 is tunneled subcutaneously toward the abdomen. Thus, the proximal spring electrode 310 comes to rest in the region of the third to seventh intercostal space 328, with the connectors 46, 52, 58, 62 positioned in the region near the stomach, as previously described.

One skilled in the art will recognize that it may be desirable to subcutaneously position electrode 310 so it lies parallel to the ribs within an intercostal space. Thus, the lead 300 will exit the subclavian vein in the region of the shoulder and be tunneled towards the abdomen. Near the desired intercostal space, the lead body 18 is curved to form a right angle so the electrode 310 rests in the desired intercostal space, parallel to the ribs. The portion of the lead body 18 proximal to the electrode 310 is also tunneled in a somewhat right angled curve, so the proximal end of the lead body 18 lies in the region of the abdomen.

Figure 12:
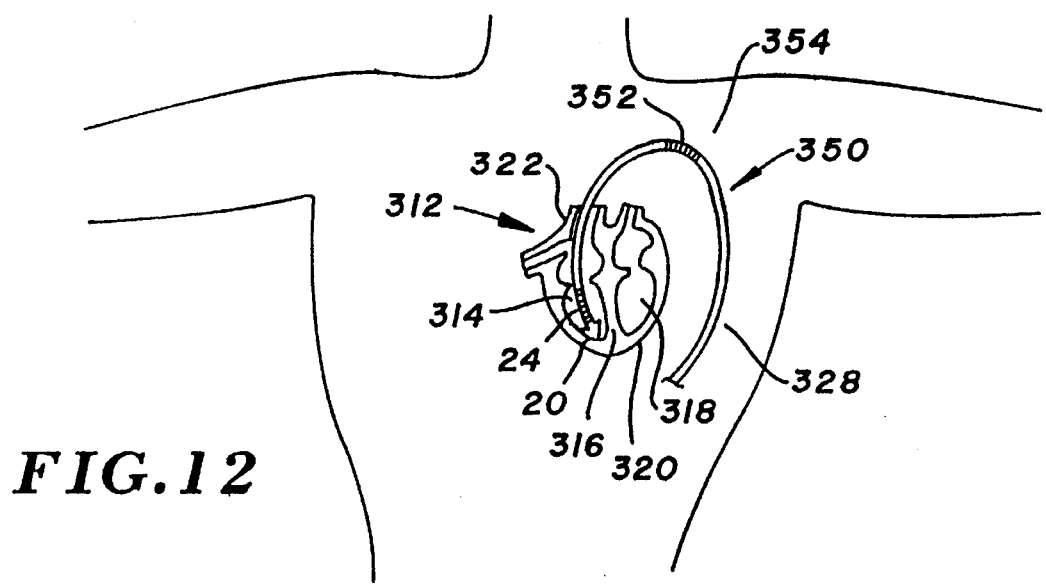
FIG. 12 is a plan view of yet another alternative embodiment of the unitary intravascular defibrillating catheter constructed in accordance with the present invention.

FIG. 12 depicts placement of an alternative embodiment of the unitary intravascular defibrillation/cardioversion catheter of the present invention. Generally depicted as 350, this embodiment features a proximal spring electrode 352 positioned in the region of the subclavian vein 354. It is contemplated that proximal electrode 352 may lie within the subclavian vein (not shown) or it may lie proximal to the point of insertion into the vein. This positioning enables a cardioverting or defibrillating shock to develop a field between distal spring electrode 24 and proximal electrode 352.

FIGS. 13, 14, 15, and 16 represent yet other variations of the catheter of the present invention. In essence, they represent a 3-electrode combination of the embodiments of FIGS. 1 or 3 plus that of FIGS. 9–11. In the embodiments described hereinafter, it is preferred that electrodes placed within the heart or the superior vena cava be sized in the range of 1.0 to 7.5 cm, as described previously. When placed in the region of the subclavian vein or subcutaneously in the region of the third through the seventh intercostal space, however, it is preferred that electrodes ranging in size from 1.0 to 25.0 cm be used, although a coil length of up to 50.0 cm is useful for some applications. An intermediate electrode is constructed similarly to proximal and distal spring electrodes 24 and 26, with a multifilar coil winding similar to conductor 60.

Figure 13:
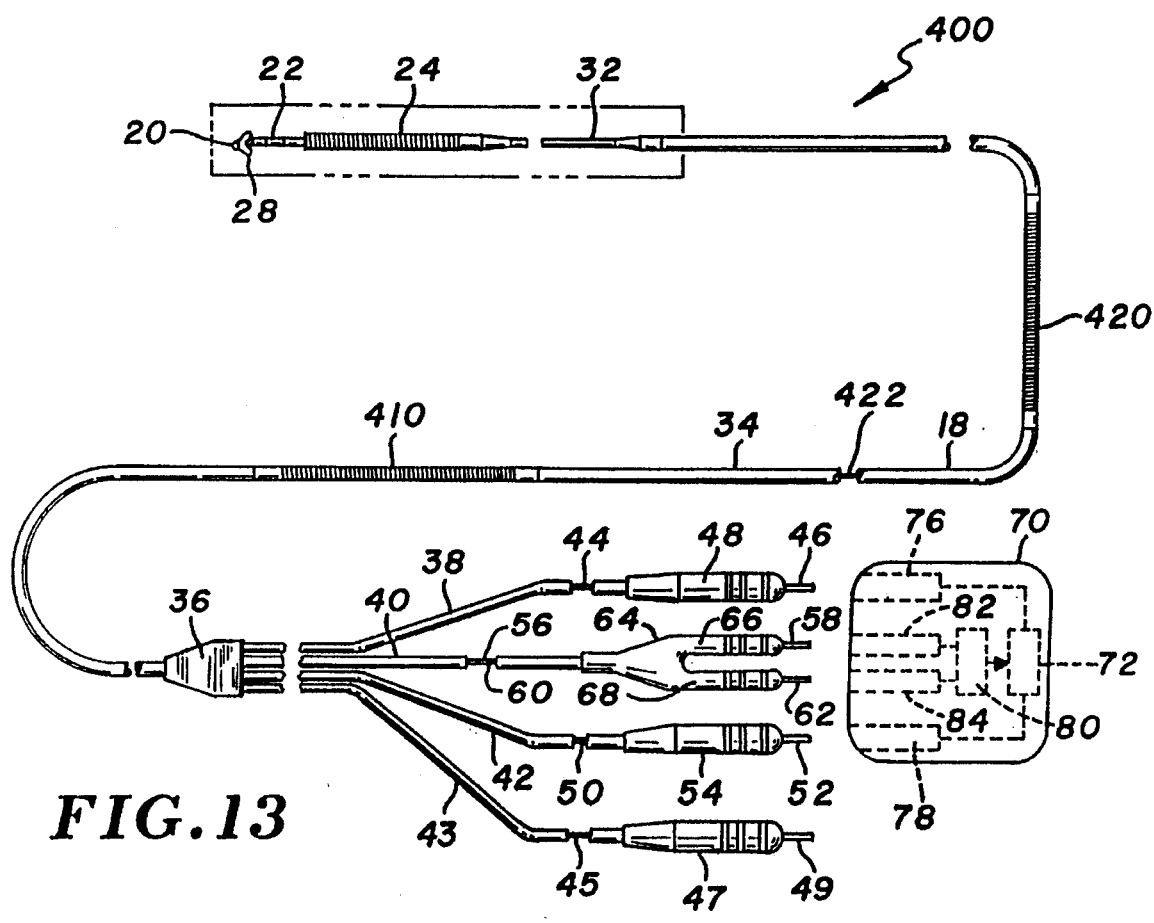
FIG. 13 is a sectional view illustrating the unitary intravascular defibrillation catheter of FIG. 12 featuring a supraventricular electrode in situ.

Referring to FIG. 13, a unitary intravascular defibrillation catheter is generally depicted as 400. The proximal spring electrode 410 is fabricated and positioned on the flexible catheter body 18 in a manner similar to the electrode 310 of FIGS. 9–11. An intermediate spring electrode 420 is interposed between distal spring electrode 24 and proximal spring electrode 410. Spring electrode 420 is constructed in a manner similar to electrode 410. A conductive wire 422 extends from reinforcing member 36 to intermediate electrode 420. An additional connector comprised of tubing 43, conductor 45, insulative boot 47 and pin 47 facilitates connection to a defibrillation unit, such as unit 70 in FIG. 1.

One skilled in the art will recognize that there exist alternative ways to selectively charge electrode 410 while electrode 420 is dormant, and vice-versa. One approach is to selectively hardwire the electrodes so the distal electrode 24 is negative while the intermediate electrode 420 and the proximal electrode 410 are positive. When hardwired in a preferred configuration, one merely connects the desired pair of electrodes to defibrillation control unit 70. Alternatively, a gatling discharge circuit may also be used, such as disclosed in Applicant's U.S. Pat. No. 4,969,463, this material being herein incorporated by reference. This gatling circuit selectively switches between electrodes during the course of the pulse.

Figure 14:
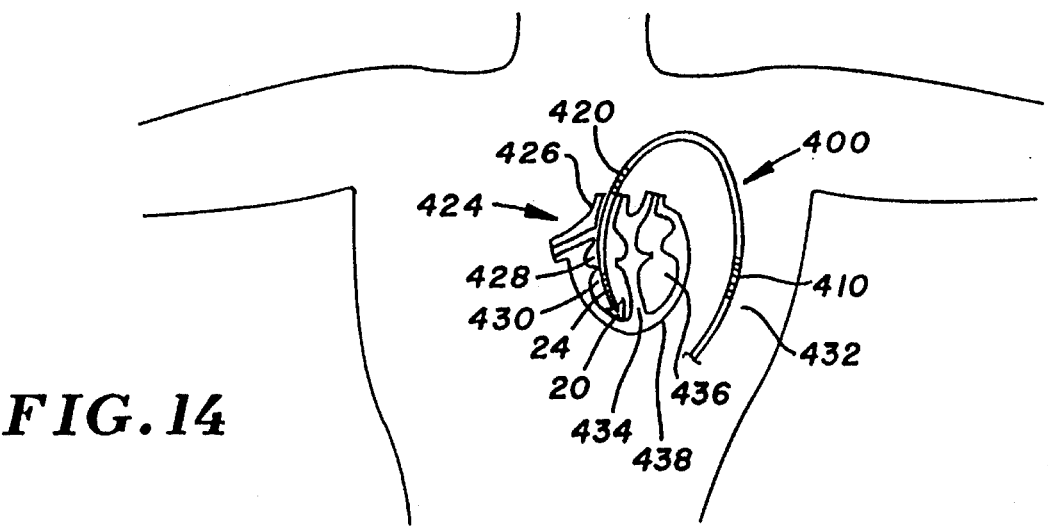
FIG. 14 is a sectional view illustrating the unitary intravascular defibrillation catheter of FIG. 12 featuring a subclavian electrode in situ.

FIG. 14 depicts an embodiment of the unitary intravascular defibrillation catheter wherein the intermediate electrode 420 is positioned within the superior vena cava. In use, catheter 400 is inserted through a slit in the subclavian vein and its distal end with distal tip electrode 20 is advanced toward the heart 424. It passes through the superior vena cava 426, the right atrium 428, and into the right ventricle 430. The distal tip electrode 20 rests at the apex of the right ventricle, as in prior embodiments. One skilled in the art will recognize that electrode 420 may alternatively be placed in the region of the right atrium 428 with substantially the same result and that catheter 400 may be configured without including the tines 28.

The proximal end of catheter 400 is tunnelled subcutaneously toward the abdomen so spring electrode 410 lies in the region of the third to seventh intercostal space 432. Precise placement of this electrode must be determined on a patient-by-patient basis to attain an optimal capture of the myocardial tissue upon receipt of a controlling signal from the defibrillation control unit 70. Alternative placement of the intermediate electrode 420 in either a superior vena cava or a subclavian position also depends upon the patient's physiology.

In use, a physician will energize distal electrode 24 to create an electronic field between the electrode 24 and either electrode 410 or 420. The field between electrodes 24 and 420 includes the apex of the right ventricle 430, the right atrial tissue 428, and the superior vena cava 426. The field between electrodes 24 and 410 includes the apex of right ventricle 430, the interventricular septum 434, the left ventricle 436, the left ventricular free wall 438, and the intercostal region 432.

Figure 15:
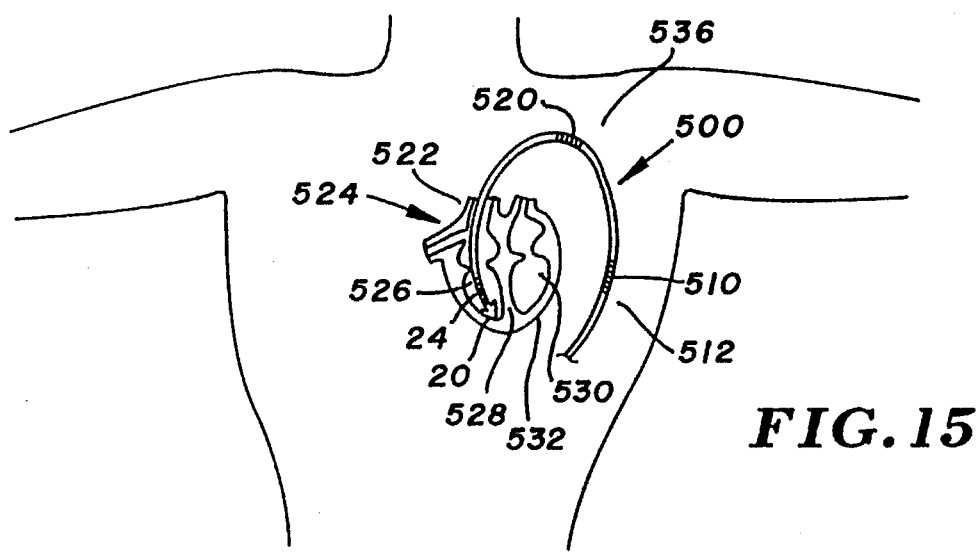
FIGS. 15 and 16 are sectional views illustrating the unitary intravascular defibrillation catheter of FIG. 12 featuring supraventricular and subclavian electrode.

Referring to FIG. 15, .the intermediate electrode may be placed outside of the superior vena cava. For example, the unitary intravascular catheter 500 is configured and dimensioned similarly to catheter 400. Thus, it includes a proximal electrode 510 positioned subcutaneously in the region of the third to seventh intercostal space 512. However, in this embodiment, the intermediate electrode 520 is positioned near or within the subclavian vein near the point of intravenous insertion. As in FIG. 14, the distal tip electrode 20 is inserted through the superior vena cava 522, the right atrium 524 and lodged within the right ventricular cavity 526. Discharge between the distal electrode 24 and proximal electrode 510 creates a field which includes the interventricular septum 528, the left ventricular cavity 530, the left ventricular free wall 532, and the intercostal region 512. Discharge between intermediate electrode 520 and electrode 24, in contrast, creates a field between the right ventricular cavity and the left ventricular septum 528, cavity 530 and free wall 532, and further including the region of the aortic root 534 and the region of subclavian placement near the shoulder 536.

As previously discussed, these electrodes may range in size from 1.0 cm to 50.0 cm. When both electrode 510 and electrode 520 are 25.0 cm in length, they provide an effective length of 50.0 cm when they are positioned adjacent one another. Because they are comprised of flexible coils, the electrode can be implanted in a U-shaped pattern. They can also be spaced a preselected distance from one another then implanted to lie parallel to one another in either the subclavian or intercostal regions.

Figure 16:
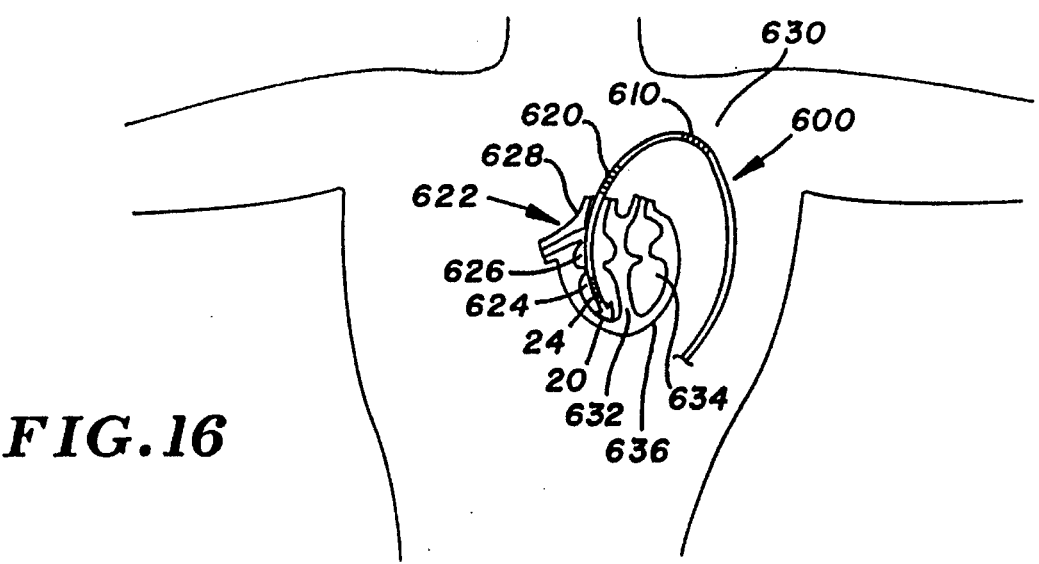

Referring now to FIG. 16, the unitary intravascular catheter 600 includes proximal electrode 610 and intermediate electrode 620 on the same catheter body 18 as distal electrode 24. When this embodiment is placed within heart 622, the tip electrode 24 is placed within the right ventricle 624. An electronic field is created between electrode 24 and electrode 620. This field includes the right atrium 626 and superior vena cava 628. Proximal electrode 610 is placed in the region of the subclavian vein 630. In this configuration, a field is created between distal electrode 24 and proximal electrode 610, which includes the interventricular septum 632, the left ventricular cavity 634 and the left ventricular free wall 636. This field causes a synchronized contraction, as in the embodiment of FIG. 15.

Although the embodiments in FIGS. 9 through 16 have been described in terms of placement in the region of the superior vena cava, the subclavian vein and the third through seventh intercostal space, the proximal and distal spring electrodes may be placed at a separation of between 10.0 cm and 60.0 cm. Additionally, the intermediate and proximal electrodes in these figures have coil lengths in the range of 1.0 to 50.0 cm. When the intermediate and the proximal spring electrodes are placed adjacent one another, an effective coil length of 100 cm is attained.

Thus, in accordance with the present invention, the R-wave sensing system is configured in complete electrical isolation from the cardioversion system, with a bipolar sensing electrode means interacting with endocardial tissue remote from tissue subject to the immediate electrical affects of cardioversion. Consequently, post-shock sensing abnormalities encountered in connection with previous devices, particularly unitary catheters, are substantially eliminated. A more timely and accurate R-wave sensing is achieved, to substantially reduce the risk of generating unnecessary and possibly harmful cardioversion pulses after a return to normal sinus rhythm. Pulses are conducted within fields created between novel placement sites along the catheter body.

What is claimed is:

1. A unitary intravascular cardioversion device for conducting electrical pulses generated by a cardioversion pulse generator, including:

an elongate, flexible and dielectric catheter body having a proximal end region and a distal end region;

a cardioversion circuit including a first cardioversion electrode mounted on said catheter body along said distal end region; a first flexible conductor means connected to said first cardioversion electrode for conducting electrical pulses between said first cardioversion electrode and said proximal end region; a second cardioversion electrode mounted on said catheter body proximally of said first cardioversion electrode, spaced apart from said first cardioversion electrode a distance selected to permit placement of the second cardioversion electrode subcutaneously within the region of the third through seventh intercostal space when the first cardioversion electrode is disposed within the right ventricular cavity; a second flexible conductor means connected to said second cardioversion electrode for transmitting electrical pulses between said second cardioversion electrode and said proximal end region; and a cardioversion connector means near said proximal end region adapted for electrically coupling said first and second conductor means with a cardioversion pulse generator to utilize said first and second cardioversion electrodes as a cardioversion electrode pair.

2. The cardioversion device of claim 1, wherein:

said first and second cardioversion electrodes, respectively, comprise distal and proximal electrically conductive coils.

3. The cardioversion device of claim 2, wherein:

each of said proximal and distal coils has a length in the range of from 1.0 to 50.0 centimeters.

4. The cardioversion device of claim 1, further including:

a cardiac sensing circuit electrically isolated from the cardioversion circuit and including a first sensing electrode mounted on said catheter body along said distal end region; a third flexible conductor means connected to said first sensing electrode for transmitting electrical pulses between said first sensing electrode and said proximal end region; a second sensing electrode, mounted on said catheter body along said distal end region proximally of said first sensing electrode and spaced apart from said first sensing electrode by a predetermined first distance; a fourth flexible conductor means connected to said second sensing electrode for transmitting electrical pulses between said second sensing electrode and said proximal end region; and a sensing connector means near said proximal end region for electrically coupling said third and fourth conductor means with a pulse sensing means.

5. The unitary intravascular cardioversion device of claim 1, wherein:

said first cardioversion electrode and said second cardioversion electrode are separated by a distance in the range of 10.0 cm through 60.0 cm.

6. The unitary, intravascular cardioversion device of claim 1, further including:

an intermediate cardioversion electrode, placed along said elongate catheter body between said first and second cardioversion electrodes; and intermediate flexible conductor means for transmitting electrical pulses between said intermediate cardioversion electrode and said proximal end region, and third cardioversion connector means disposed near said proximal end region for electrically coupling said intermediate conductor means with a cardioversion pulse generator.

7. The unitary intravascular cardioversion device of claim 6, wherein:

at least one of said first, second and intermediate flexible conductor means comprises an electrically conductive coil winding housed within a lumen means of said catheter body.

8. The unitary intravascular cardioversion device of claim 6, wherein at least one of said first, second and intermediate flexible conductor means is comprised of a plurality of filaments embedded in said catheter body.

9. The unitary, intravascular cardioversion device of claim 1, further including:

an intermediate cardioversion electrode disposed on said catheter body between said first and second cardioversion electrodes and positioned within the superior vena cava when said first cardioversion electrode is disposed within the cavity of the right ventricle, and further including intermediate flexible conductor means for transmitting electrical pulses between said intermediate cardioversion electrode and said proximal end region, and third cardioversion connector means disposed near said proximal end region adapted for electrically coupling said intermediate conductor means with a cardioversion pulse generator.

10. The unitary, intravascular cardioversion device of claim 1, further including:

an intermediate cardioversion electrode disposed on said catheter body between said first and second cardioversion electrodes and positioned within the region of the subclavian vein when said first cardioversion electrode is disposed within the cavity of the right ventricle, and further including intermediate flexible conductor means for transmitting electrical pulses between said intermediate cardioversion electrode and said proximal end region, and third cardioversion connector means near said proximal end region for electrically coupling said third conductor means with said cardioversion pulse generating means.

11. The unitary intravascular cardioversion device of claim 1, wherein:

said catheter body further is adapted for positioning the second cardioversion electrode in a selected intercostal space and aligned parallel to the ribs.

12. A defibrillator catheter comprising:

an elongate catheter body comprised of a flexible and dielectric material, and having a proximal end and a distal end;

a sensing electrode mounted to said catheter proximate said distal end;

a first defibrillating electrode mounted to said catheter body at a selected distance proximally of said sensing electrode, and a second defibrillating electrode mounted proximally of said first defibrillating electrode and spaced apart from said first defibrillating electrode by a distance substantially more than ten cm and at least sufficient to permit placement of the second defibrillating electrode in the region of the subclavian vein when the first defibrillation electrode is within the right ventricular cavity;

first, second and third flexible conductor means connected, respectively, to said sensing electrode, first defibrillating electrode and second defibrillating electrode, said conductor means electrically isolated from one another;

a first and second defibrillator connector means adapted for electrically coupling said second and third conductor means to a defibrillation pulse generator to form a defibrillation circuit which further includes said defibrillation electrodes; and a sensing connector means adapted for electrically coupling said first conductor means with cardiac sensing circuitry to form pulse sensing circuitry.

13. The defibrillator catheter of claim 12, wherein:

separation between said first and second defibrillating electrodes is selected to position said second defibrillating electrode within the subcutaneous region approximately at the third through seventh intercostal space when said first defibrillation electrode is positioned within the right ventricular cavity.

14. The defibrillator catheter of claim 13, further including:

an intermediate defibrillating electrode, placed along said elongate catheter body between said first and second defibrillating electrodes;

intermediate flexible conductor means for transmitting electrical pulses between said intermediate defibrillating electrode and said proximal end; and third defibrillator connector means near said proximal end of said catheter body for electrically coupling said intermediate conductor means with a defibrillation pulse generator.

15. The defibrillator catheter of claim 13, further including:

an intermediate defibrillating electrode proximally separated from said first defibrillating electrode by a distance selected to permit placement of said intermediate defibrillating electrode within the superior vena cava when said first defibrillating electrode is positioned within the right ventricular cavity;

fourth flexible conductor means for transmitting electrical pulses between said intermediate defibrillating electrode and said proximal end; and third defibrillator connector means near said proximal end of said catheter body for electrically coupling said fourth conductor means with a defibrillation pulse generator.

16. The defibrillator catheter of claim 15, wherein:

at least one of said first, second, third and fourth flexible conductor means is comprised of an electrically conductive coil winding housed in a dielectric sheath and contained within a lumen means of said catheter body.

17. The defibrillator catheter of claim 13, further including:

an intermediate defibrillating electrode proximally separated from said first defibrillating electrode by a distance selected to permit placement of said intermediate defibrillating electrode within the region of the subclavian vein when said first defibrillating electrode is positioned within the cavity of the right ventricle;

fourth flexible conductor means for transmitting electrical pulses between said intermediate defibrillating electrode and said proximal end; and third defibrillator connector means near said proximal end of said catheter body for electrically coupling said fourth conductor means with a defibrillation pulse generator.

18. The defibrillator catheter of claim 17, wherein:

at least one of said first, second, third and fourth flexible conductor means is embedded in said catheter body and is comprised of an electrically conductive coil winding.

19. The defibrillator catheter of claim 13 wherein:

said catheter body further is adapted for positioning the second defibrillating electrode in a selected intercostal space and aligned parallel to the ribs.

20. The defibrillator catheter of claim 12, further including:

an intermediate defibrillating electrode, placed along said elongate catheter body between said first and second defibrillating electrodes;

an intermediate flexible conductor means embedded in said catheter body for transmitting electrical pulses between and third defibrillator connector means near said proximal end of said catheter body for electrically coupling said intermediate conductor means with a defibrillation pulse generator.

21. The defibrillator catheter of claim 12, further including:

a third defibrillating electrode separated from said first defibrillating electrode by a distance selected to permit placement of said third defibrillating electrode within the superior vena cava when said first defibrillating electrode is positioned within the right ventricular cavity, and said second defibrillating electrode is positioned in the region of the subclavian vein;

fourth flexible conductor means embedded in said catheter body for transmitting electrical pulses between said third defibrillating electrode and said proximal end; and third defibrillator connector means near said proximal end of said catheter body for electrically coupling said fourth conductor means with a defibrillation pulse generator.

22. A transvenous defibrillating catheter, insertable into a right ventricle of a heart by way of a superior vena cava, comprising:

an elongate catheter body comprised of a flexible and dielectric material and having a proximal end, a distal end and a lumen means running substantially the length of the catheter body from the proximal end to said distal end;

a distal sensing electrode mounted to said catheter at least proximate said distal end;

a defibrillating electrode means mounted to said catheter body proximally of said distal sensing electrode, said defibrillating electrode means including a distal defibrillating electrode surface area at least three times the surface area of the distal sensing electrode and mounted to the catheter body, and a proximal defibrillating electrode having a surface area at least three times the surface area of the distal sensing electrode and spaced apart from the distal defibrillating electrode a distance at least sufficient to permit placement of the proximal defibrillating electrode in the region of the subclavian vein when the distal defibrillating electrode is within the right ventricular cavity, and a defibrillator conductor means electrically coupled to said defibrillating electrode means and adapted for coupling to a defibrillation pulse generator, for transmitting defibrillation pulses between a defibrillation pulse generator and said defibrillating electrodes;

a sensing conductor connected to said distal sensing electrode for transmitting electrical signals between said proximal end of the catheter body and said distal sensing electrode said sensing conductor being electrically isolated from said defibrillator conductor means; and a sensing connector means adapted for electrically coupling said sensing conductor with a cardiac sensing circuit to form a pulse sensing means.

23. The transvenous defibrillator catheter of claim 22, wherein:

said proximal defibrillating electrode is positioned a distance from said distal defibrillating electrode in the range of 10.0 cm through 60.0 cm.

24. The transvenous defibrillator catheter of claim 22, wherein:

separation between said proximal and distal defibrillating electrodes is selected to enable positioning said proximal defibrillating electrode within the subcutaneous region approximately at the third through seventh intercostal space when said distal end of said transvenous defibrillator catheter is positioned within the right ventricular cavity.

25. The transvenous defibrillator catheter of claim 24, further including:

an intermediate defibrillating electrode, placed along said elongate catheter body between said proximal and distal defibrillating electrodes; and intermediate defibrillator conductor means electrically coupled to said intermediate defibrillating electrode for transmitting defibrillation pulses between said defibrillation pulse generating means near said proximal end of said catheter body and said intermediate defibrillating electrode.

26. The transvenous defibrillator catheter of claim 25, wherein:

separation between said intermediate defibrillating electrode and said defibrillation pulse generator means is selected to position said intermediate defibrillating electrode within the region of the superior vena cava.

27. The transvenous defibrillator catheter of claim 25, wherein:

separation between said intermediate defibrillating electrode and said defibrillation pulse generator means is selected to position said intermediate defibrillating electrode within the region of the subclavian vein.

28. The transvenous defibrillating catheter of claim 24, wherein:

said catheter body further is adapted for positioning the proximal defibrillating electrode in a selected intercostal space and aligned parallel to the ribs.

29. The transvenous defibrillator catheter of claim 22, further including:

an intermediate defibrillating electrode, placed along said elongate catheter body between said proximal and distal defibrillating electrodes; and intermediate defibrillator conductor means electrically coupled to said intermediate defibrillating electrode for transmitting pulses between said defibrillation proximal end of said catheter body and said intermediate defibrillating electrode.

30. The transvenous defibrillator catheter of claim 29, wherein:

separation between said intermediate defibrillating electrode and said defibrillation pulse generator means is selected to position said intermediate defibrillating electrode within the region of the superior vena cava.

31. A unitary intravascular cardioversion for conducting electrical pulses generated by a cardioversion generator, including:

an elongate, flexible and dielectric catheter body having a proximal end region and a distal end region;

a cardioversion circuit including a first cardioversion electrode mounted on said catheter body along said distal end region; a first flexible conductor means connected to said first cardioversion electrode for conducting electrical pulses between said first cardioversion electrode and said proximal end region; a second cardioversion electrode mounted on said catheter body proximally of said first cardioversion electrode, spaced apart from said first cardioversion electrode a distance substantially more than ten cm and selected to enable positioning of said second cardioversion electrode within the region of the subclavian vein when said first cardioversion electrode is disposed within the cavity of the right ventricle; a second flexible conductor means connected to said second cardioversion electrode for transmitting electrical pulses between said second cardioversion electrode and said proximal end region; and a cardioversion connector means near said proximal end region adapted for electrically coupling said first and second conductor means with a cardioversion pulse generator, thereby to utilize said first and second cardioversion electrodes as a cardioversion electrode pair.

32. The unitary intravascular cardioversion device of claim 31, further including:

an intermediate cardioversion electrode, placed along said elongate catheter body between said first and second cardioversion electrodes; and intermediate flexible conductor means for transmitting electrical pulses between said intermediate cardioversion electrode and said proximal end region, and third cardioversion connector means near said proximal end region for electrically coupling said intermediate conductor means with a cardioversion pulse generator.

33. The unitary intravascular cardioversion device of claim 32 wherein:

at least one of said first, second and intermediate flexible conductor means comprises an electrically conductive coil winding housed within a lumen means of said catheter body.

34. The unitary intravascular cardioversion device of claim 32, wherein:

at least one of said first, second and intermediate flexible conductor means is comprised of a plurality of filaments embedded in said catheter body.

35. The unitary intravascular cardioversion device of claim 31 further including:

an intermediate cardioversion electrode disposed on said catheter body between said first and second cardioversion electrodes and positioned within the superior vena cava when said first cardioversion electrode is disposed within the cavity of the right ventricle, intermediate flexible conductor means for transmitting electrical pulses between said intermediate cardioversion electrode and said proximal end region, and third cardioversion connector means near said proximal end region for electrically coupling said intermediate conductor means with a cardioversion pulse generator.

36. The unitary intravascular cardioversion device of claim 31 further including:

a first cardiac sensing electrode mounted on said catheter along the distal end region, spaced apart distally of and electrically isolated from the first cardioversion electrode;

a third flexible conductor means connected to the first cardiac sensing electrode, for transmitting electrical pulses between the first cardiac sensing electrode and said proximal end region, said first, second and third flexible conductor means being electrically isolated from one another; and a cardiac sensing connector means near said proximal end region for electrically coupling said third conductor means with a pulse sensing means.

37. The unitary intravascular cardioversion device of claim 36 further including:

a second cardiac sensing electrode mounted on said catheter body along said distal end region, between the first cardiac sensing electrode and the first cardioversion electrode, said second cardiac sensing electrode being spaced apart from and electrically isolated from the first cardiac sensing electrode and the first cardioversion electrode;

a fourth flexible conductor means connected to the second cardiac sensing electrode, for transmitting electrical pulses between the second cardiac sensing electrode and said proximal end region, said fourth flexible conductor means being electrically isolated from the first, second and third flexible conductor means; and wherein said sensing connector means further electrically couples said fourth flexible conductor means with the pulse sensing means.

38. The unitary intravascular cardioversion device of claim 36 wherein:

said third flexible conductor means comprises an electrically conductive coil winding housed within a lumen means of said catheter body.

* * * * *

UNITED STATES PATENT AND TRADEMARK OFFICE
CERTIFICATE OF CORRECTION

PATENT NO. : 5,545,205
DATED : August 13, 1996
INVENTOR(S) : Theodore J. Schulte, et al It is certified that error appears in the above-indentified patent and that said Letters Patent is hereby corrected as shown below:

Claim 10, column 15, line 26 after "region" insert
-- adapted --; line 27 delete "said", second occurrence,
and insert -- a --; line 28 delete "generating means"
and insert -- generator --.

Claim 20, column 16, line 67 after "between" insert -- said
intermediate defibrillating electrode and said proximal end; --

Claim 22, column 17, line 34 after "electrode" insert
-- having a --.

Claim 29, column 18, line 42 after "transmitting" insert
-- defibrillation --; same line after "said" delete
-- defibrillation --.

Signed and Sealed this

Twelfth Day of November, 1996

*Attest:*

BRUCE LEHMAN

*Attesting Officer*    *Commissioner of Patents and Trademarks*